United States Patent
Liu et al.

(10) Patent No.: US 11,781,864 B1
(45) Date of Patent: Oct. 10, 2023

(54) METHOD AND SYSTEM FOR SURVEY AND STABILITY EVALUATION OF UPSTREAM TAILING FILL DAM

(71) Applicant: Kunming Prospecting Design Institute Of China Nonferrous Metals Industry Co., Ltd., Kunming (CN)

(72) Inventors: Wenlian Liu, Kunming (CN); Sugang Sui, Kunming (CN); Shaowei Yu, Kunming (CN); Peng Li, Kunming (CN); Hanhua Xu, Kunming (CN); Bangtuan Wang, Kunming (CN); Pengfei Xu, Kunming (CN); Pengwei Han, Kunming (CN)

(73) Assignee: Kunming Prospecting Design Institute Of China Nonferrous Metals Industry Co., Ltd., Kunming (CN)

( * ) Notice: Subject to any disclaimer, the term of this patent is extended or adjusted under 35 U.S.C. 154(b) by 0 days.

(21) Appl. No.: 18/312,080

(22) Filed: May 4, 2023

(30) Foreign Application Priority Data

Sep. 1, 2022 (CN) .......................... 202211062766.3

(51) Int. Cl.
*E02B 7/06* (2006.01)
*G01C 15/00* (2006.01)
(Continued)

(52) U.S. Cl.
CPC ............. *G01C 15/002* (2013.01); *E02B 7/06* (2013.01); *G01C 13/002* (2013.01); *G01C 15/02* (2013.01); *G01N 33/24* (2013.01)

(58) Field of Classification Search
None
See application file for complete search history.

(56) References Cited

U.S. PATENT DOCUMENTS 9,394,786 B2 * 7/2016 Duran Toro .......... E21B 49/005
9,989,664 B2 * 6/2018 Campbell ................ G01V 3/20
(Continued)

FOREIGN PATENT DOCUMENTS

CN 103530465 A 1/2014
CN 106192910 A * 12/2016 ............... E02B 7/06
(Continued)

OTHER PUBLICATIONS

Liu Wenlian et al, A Preliminary Study of New Prospecting Technology of Large Tailings—Dam and Engineering Property of Tailings, Journal of Engineering Geology, Jun. 30, 2004, p. 523-528.
(Continued)

*Primary Examiner* — Christopher W Fulton
(74) *Attorney, Agent, or Firm* — Zhigang Ma

(57) ABSTRACT

The present disclosure relates to the field of survey and stability evaluation of a tailing fill dam, in particular to a method and system for survey and stability evaluation of an upstream tailing fill dam, wherein the method comprises the following steps: selecting a drill bit and a soil sampler for a target tailing fill dam; collecting tailing sand at different depths of the target tailing fill dam using the drill bit and the soil sampler; detecting an undisturbed soil sample of the tailing sand; setting a preset standard according to the undisturbed soil sample, and screening the tailing sand using the preset standard to obtain a tailing sand sample; detecting the particle composition of the tailing sand sample; detecting the mechanical property of the tailing sand sample; and evaluating the stability of the target tailing fill dam through the particle composition and the mechanical property.

12 Claims, 11 Drawing Sheets

(51) Int. Cl.
      *G01C 15/02*       (2006.01)
      *G01N 33/24*       (2006.01)
      *G01C 13/00*       (2006.01)

(56) References Cited

U.S. PATENT DOCUMENTS

| | | | |
|---|---|---|---|
| 11,072,905 B2 * | 7/2021 | Hull | C04B 30/02 |
| 2020/0283324 A1 * | 9/2020 | Filmer | B09B 1/00 |
| 2021/0156810 A1 * | 5/2021 | Botto | G01N 23/02 |

FOREIGN PATENT DOCUMENTS

| | | | |
|---|---|---|---|
| CN | 112523176 A | * | 3/2021 |
| CN | 113293739 A | * | 8/2021 |

OTHER PUBLICATIONS

CNIPA, Notification of a First Office Action for CN202211062766.3, dated Oct. 13, 2022.
CNIPA, Notification to grant patent right for invention in CN202211062766.3, dated Oct. 22, 2022.

\* cited by examiner

METHOD AND SYSTEM FOR SURVEY AND STABILITY EVALUATION OF UPSTREAM TAILING FILL DAM

TECHNICAL FIELD

The present disclosure relates to the field of survey and stability evaluation of a tailing fill dam, in particular to a method and system for survey and stability evaluation of an upstream tailing fill dam.

BACKGROUND

The part of the product in the sorting operation of mineral separation which cannot be used for production because of the low content of a useful target component is referred to as tailings. The dam built by a reservoir storing various tailings is referred to as a tailing fill dam. The tailing fill dam is mainly categorized as an upstream tailing fill dam, a midline tailing fill dam and a downstream tailing fill dam. For the midline tailing fill dam and the downstream tailing fill dam, the fill dam body consists of coarse-particle tailings which are manually controlled and sorted. The fill dam body has a clear outline, which makes the boundary between fine-particle tailings and coarse-particle tailings filled (deposited) in the reservoir basically well-defined. The fill dam body of the upstream tailing fill dam is integrated with tailings formed by natural deposition of tailing particles in flowing pulp. The boundary between coarse-particle tailings of the fill dam body is basically blurred. At the same time, due to the short time of tailing fill and the poor strength of the intergranular structure, the hole wall is easy to collapse during drilling, and the drilling efficiency is low. Moreover, different kinds of ores with different structures require different mineral separation processes, and the tailings produced by different mineral separation processes often have certain differences in technological properties, especially in particle shape and particle size distribution, which further hinders the survey of the upstream tailing fill dam and the stability evaluation of the dam body. Therefore, there is an urgent need for a method and system for survey and stability evaluation of an upstream tailing fill dam to grasp the actual state of the upstream tailing fill dam and the stability state of the dam body.

SUMMARY

Aiming at the shortcomings in the prior art and the actual engineering requirements, in a first aspect, the present disclosure provides a method for survey and stability evaluation of an upstream tailing fill dam, comprising the following steps: selecting a drill bit and a soil sampler for a target tailing fill dam; collecting tailing sand at different depths of the target tailing fill dam using the drill bit and the soil sampler; detecting an undisturbed soil sample of the tailing sand; setting a preset standard according to the undisturbed soil sample, and screening the tailing sand using the preset standard to obtain a tailing sand sample; detecting particle composition of the tailing sand sample, wherein the particle composition comprises the diameter size of particles forming the tailing sand and the number of particles of the tailing sand in different particle diameter ranges; detecting the mechanical property of the tailing sand sample, wherein the mechanical property comprises cohesion, friction strength and shear strength of the tailing sand sample; and evaluating the stability of the target tailing fill dam through the particle composition and the mechanical property.

According to the present disclosure, a drill bit and a soil sampler which are appropriate are selected for the target tailing fill dam to collect the actual tailing sand, so that the sampling resistance resulted from the difference of particle shapes and particle compositions of different tailing fill dams is weakened. Meanwhile, the accuracy of subsequent analysis of the tailing sand is ensured by detecting an undisturbed soil sample of the collected tailing sand. The corresponding target tailing fill dam is evaluated by constructing a stability evaluation function from the actually collected parameters, so that the evaluation quality is ensured. Through the present disclosure, the actual state and the stability state of the upstream tailing fill dam can be mastered, which provides a basis for correctly managing the upstream tailing fill dam, handling tailing accidents, maintaining the upstream tailing fill dam and the like. In addition, the present disclosure can also find the abnormal signs of the upstream tailing fill dam in time, and analyze the reasons according to the relevant data, so as to take timely measures to prevent the upstream tailing fill dam from accidents.

Preferably, the method for survey and stability evaluation of the upstream tailing fill dam according to the present disclosure further comprises the following steps: simulating a frost heaving condition of the tailing sand sample at different depths at different temperatures; measuring water content of the tailing sand sample; obtaining preservation temperature by combining the water content with the frost heaving condition; and setting the preservation temperature to preserve the tailing sand sample. Due to the limitation of field conditions, hundreds of undisturbed tailing soil samples need to be transported to an indoor laboratory for experiment. It is a difficult problem to keep the undisturbed samples in long-distance transportation because of the low strength of the intergranular structure of the tailing sand. In the present disclosure, the preservation temperature suitable for tailing sand samples is obtained by simulating the frost heaving condition of tailing sand samples at different temperatures, so as to preserve tailing sand samples.

Preferably, selecting the drill bit and the soil sampler for the target tailing fill dam comprises the following steps: simulating a core recovery success rate, a core recovery rate, a difficulty degree of drilling operation and a drilling condition of different drilling technologies for the target tailing fill dam, wherein the different drilling technologies comprise impact drilling, reverse circulation drilling, pumpless reverse circulation drilling, auger drilling and auger pumpless reverse circulation drilling; selecting an optimal drilling mode according to the core recovery success rate, the core recovery rate, the difficulty degree of drilling operation and the drilling condition, and selecting a corresponding drill bit according to the optimal drilling mode; simulating a relationship function between a soil sampling area of the soil sampler, a soil sampling length of the soil sampler, a soil sampling mode of the soil sampler and a soil sampling recovery rate of the soil sampler for the target tailing fill dam; designing an optimal parameter of the soil sampler according to the relationship function, and selecting the corresponding soil sampler according to the optimal parameter.

Preferably, collecting tailing sand at different depths of the target tailing fill dam using the drill bit and the soil sampler comprises the following steps: drilling holes by auger drilling using the drill bit above an immersion line to generate shallow tailing sampling points; collecting tailing sand in the shallow tailing sampling points using the soil sampler; drilling holes by auger pumpless reverse circulation drilling using the drill bit below the immersion line to generate deep tailing sampling points; collecting tailing sand in the deep tailing sampling points using the soil sampler;

Preferably, detecting an undisturbed soil sample of the tailing sand comprises the following steps: presetting the characteristics of the tailing sand according to the structure of the soil sampler, wherein the characteristics comprise a preset volume and a preset surface area of the tailing sand; using the characteristics to construct an initial undisturbed soil sample judging model; measuring the tailing sand to obtain a measured volume and a measured surface area; preliminarily judging the undisturbed soil sample of the tailing sand according to the measured volume, the measured surface area and the initial undisturbed soil sample judging model; measuring a volumetric strain of the tailing sand at different depths; using the volumetric strain of the tailing sand to fit a tailing sand volumetric strain-depth regression curve equation; judging the undisturbed soil sample of the tailing sand again using the tailing sand volumetric strain-depth regression curve equation.

Further preferably, the initial undisturbed soil sample judging model satisfies the following formula:

$$C = \text{average}(S'/S, V'/V),$$

where C represents the degree of the initial undisturbed soil sample of the tailing sand, S' represents the measured surface area of the tailing sand, S represents the preset surface area of the tailing sand, V' represents the measured volume of the tailing sand, and V represents the preset volume of the tailing sand.

Further preferably, the tailing sand volumetric strain-depth regression curve equation comprises:

a tailing fine sand volumetric strain-depth regression curve equation: $\varepsilon_v = 0.5409 \ln h + 0.6636$;

a tailing powder sand volumetric strain-depth regression curve equation: $\varepsilon_v = 0.4137 \ln h + 0.8021$;

a tailing powder soil volumetric strain-depth regression curve equation: $\varepsilon_v = 0.5024 \ln h + 0.5284$;

where $\varepsilon_v$ represents a volumetric strain value, and h represents the depth of the tailing sand.

Preferably, the preset standard comprises an upper boundary curve equation and a lower boundary curve equation.

The upper boundary curve equation comprises:

a tailing fine sand upper boundary curve equation: $\varepsilon_v = 0.7855 \ln h + 0.8013$;

a tailing powder sand upper boundary curve equation: $\varepsilon_v = 0.5177 \ln h + 0.9215$;

a tailing powder soil upper boundary curve equation: $\varepsilon_v = 0.6451 \ln h + 1.0253$;

the lower boundary curve equation comprises:

a tailing fine sand lower boundary curve equation: $\varepsilon_v = 0.3118 \ln h + 0.5081$;

a tailing powder sand lower boundary curve equation: $\varepsilon_v = 0.3462 \ln h + 0.6675$;

a tailing powder soil lower boundary curve equation: $\varepsilon_v = 0.3788 \ln h + 0.7133$;

where $\varepsilon_v$ represents a volumetric strain value, and h represents the depth of the tailing sand.

Preferably, evaluating the stability of the target tailing fill dam through the particle composition and the mechanical property comprises the following steps: generating a particle accumulation profile according to the particle composition in combination with a deposition law, wherein the particle accumulation profile comprises an initial dam, a fill dam slope surface, a beach surface, an immersion line, a first particle area, a second particle area, a third particle area and a water storage area; building a consolidation accumulation profile according to the mechanical property in combination with a tailing discharge mode, wherein the consolidation accumulation profile comprises an initial dam, a fill dam slope surface, a beach surface, an immersion line, a first consolidation area, a second consolidation area, a third consolidation area and a water storage area; extracting first parameter information of a first particle area, a second particle area and a third particle area in the particle accumulation profile, wherein the first parameter information comprises particle distribution area size, particle component and particle distribution position; extracting second parameter information of the first consolidation area, the second consolidation area and the third consolidation area in the consolidation accumulation profile, wherein the second parameter information comprises the mechanical property of consolidation, the area size of the same consolidation mode and the distribution position of the same consolidation mode; constructing a stability evaluation function by combining the first parameter information with the second parameter information, and evaluating the stability of the target tailing fill dam using the stability evaluation function.

Further preferably, the stability evaluation function satisfies the following formula:

$$E = \begin{cases} 1 - \dfrac{s_a/s_B}{s_b/s_B} - \dfrac{s_b}{s_B} \cdot e^{-\frac{f-\mu}{\tau_f - \mu}}, & (\alpha K_{Aa}, \beta K_{Bb}, \gamma K_{Cc})_{max} = \alpha K_{Aa} \\ 1 - \dfrac{S_a}{S_A} \cdot \left( \dfrac{f-\mu}{\tau_f - \mu} + \omega \right), & (\alpha K_{Aa}, \beta K_{Bb}, \gamma K_{Cc})_{max} = \beta K_{Bb} \\ \dfrac{s_b/s_C}{s_c/s_C} + \dfrac{s_c}{s_C} \cdot e^{-1/\omega}, & (\alpha K_{Aa}, \beta K_{Bb}, \gamma K_{Cc})_{max} = \gamma K_{Cc} \end{cases}$$

where $E \in (0,1)$, E represents the stability of the target tailing fill dam, $S_a$ represents the area of the first particle area, $S_b$ represents the area of the second particle area, $S_c$ represents the area of the third particle area, $S_A$ represents the area of the first consolidation area, $S_B$ represents the area of the second consolidation area, $S_C$ represents the area of the third consolidation area, f represents the cohesion of the tailing sand sample, $\tau_f$ represents the shear strength of the tailing sand sample, $\mu$ represents the stress correction of the tailing sand sample, $\omega$ represents the friction strength coefficient of the tailing sand sample, $K_{Aa}$ represents the proportion of the area of the first particle area in the area of the first consolidation area, $\alpha$ represents the normalization coefficient of $K_{Aa}$, $K_{Bb}$ represents the proportion of the area of the second particle area in the area of the second consolidation area, $\beta$ represents the normalization coefficient of $K_{Bb}$, $K_{Cc}$ represents the proportion of the area of the third particle area in the area of the third consolidation area, and $\gamma$ represents the normalization coefficient of $K_{Cc}$.

In a second aspect, the present disclosure further provides a system for survey and stability evaluation of an upstream tailing fill dam, wherein the system for survey and stability evaluation of the upstream tailing fill dam is suitable for the method for survey and stability evaluation of the upstream tailing fill dam described in the first aspect, comprising: a soil sampling device module, which is configured to select a drill bit and a soil sampler for a target tailing fill dam; a tailing sampling module, which is configured to collect tailing sand at different depths of the target tailing fill dam using the drill bit and the soil sampler; a sample detecting module, which is configured to detect an undisturbed soil sample, particle composition and mechanical property of the tailing sand; a sample screening module, which is configured to set a preset standard according to the undisturbed soil sample, and screen the tailing sand using the preset standard to obtain a tailing sand sample; a sample preserving module, which is configured to preserve the tailing sand sample; a tailing dam analyzing module, which is configured to evaluate the stability of the target tailing fill dam through the particle composition and the mechanical property. Through the cooperation of a plurality of functional modules, the present disclosure realizes the stable implementation of the method for survey and stability evaluation of the upstream tailing fill dam, has strong robustness, and improves the practical benefit and commercial value of the present disclosure. At the same time, the present disclosure further provides tools for correctly managing the upstream tailing fill dam, handling tailing accidents, maintaining the upstream tailing fill dam and the like.

DETAILED DESCRIPTION OF THE EMBODIMENTS

Hereinafter, specific embodiments of the present disclosure will be described in detail. It should be noted that the embodiments described here are only for illustration, rather than limit the present disclosure. In the following description, numerous specific details are set forth in order to provide a thorough understanding of the present disclosure. However, it will be apparent to those skilled in the art that these specific details are not necessary to practice the present disclosure. In other instances, well-known circuits, software or methods have not been described in detail in order to avoid obscuring the present disclosure.

Throughout the specification, references to "one embodiment", "an embodiment", "one example" or "an example" mean that a particular feature, structure or characteristic described in connection with the embodiment or example is included in at least one embodiment of the present disclosure. Therefore, the phrases "in one embodiment", "in an embodiment", "one example" or "an example" appearing in various places throughout the specification do not necessarily all refer to the same embodiment or example. Furthermore, the particular feature, structure or characteristic may be combined in one or more embodiments or examples in any suitable combination and/or sub-combination. In addition, it should be understood by those skilled in the art that the drawings provided herein are for illustration purposes and are not necessarily drawn to scale.

Figure 1:
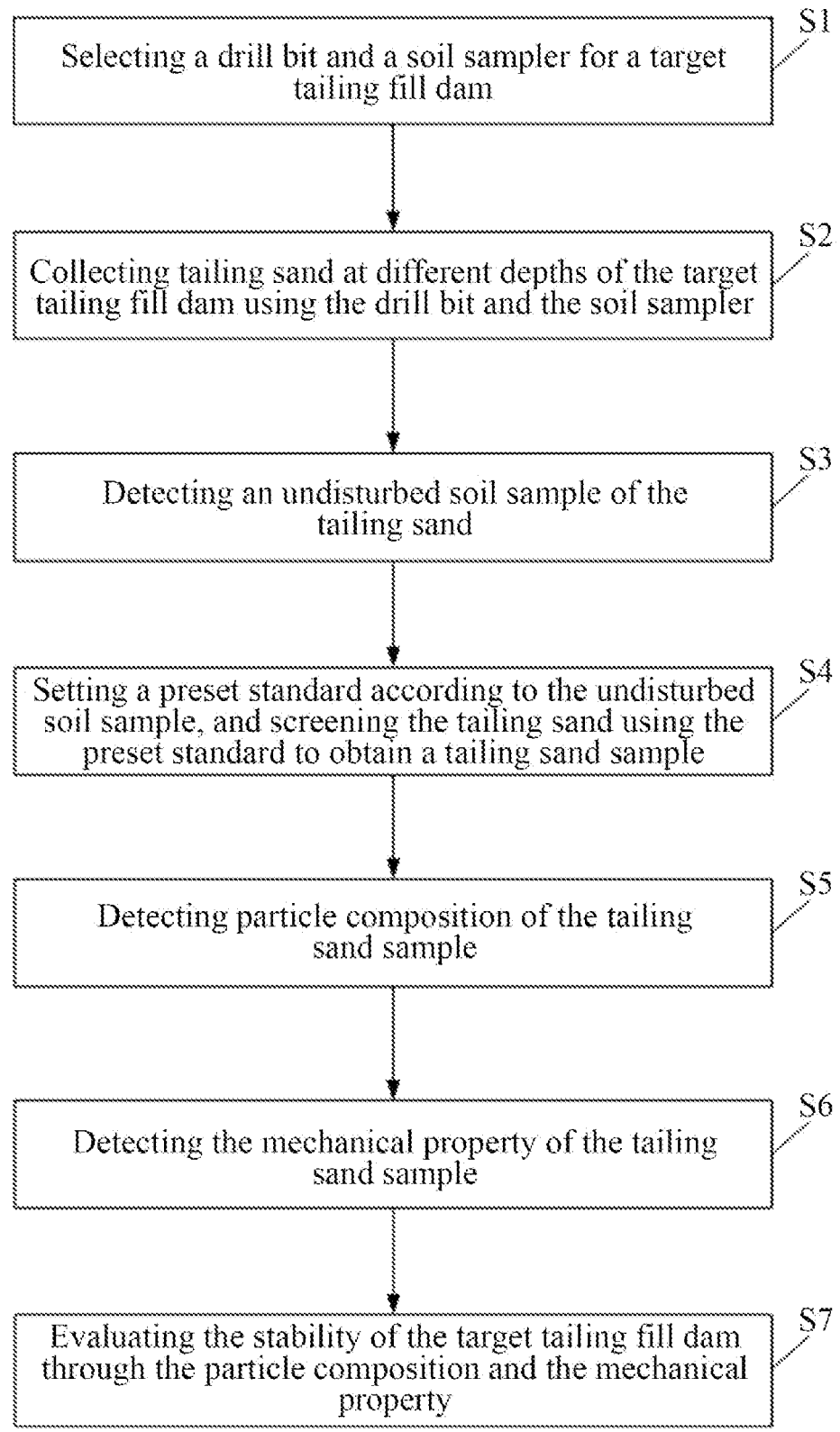
FIG. 1 is a flow chart of a method for survey and stability evaluation of an upstream tailing fill dam according to the present disclosure.

In one embodiment, as shown in FIG. 1, the present disclosure provides a method for survey and stability evaluation of an upstream tailing fill dam, which comprises the following steps.

S1, a drill bit and a soil sampler are selected for a target tailing fill dam.

In an alternative embodiment, selecting the drill bit and the soil sampler for the target tailing fill dam comprises the following steps: simulating a core recovery success rate, a core recovery rate, a difficulty degree of drilling operation and a drilling condition of different drilling technologies for the target tailing fill dam, wherein the different drilling technologies comprise impact drilling, reverse circulation drilling, pumpless reverse circulation drilling, auger drilling and auger pumpless reverse circulation drilling; selecting an optimal drilling mode according to the core recovery success rate, the core recovery rate, the difficulty degree of drilling operation and the drilling condition, and selecting a corresponding drill bit according to the optimal drilling mode; simulating the relationship between the area ratio of the soil sampler, the pipe shoe length of the soil sampler, the soil sampling mode of the soil sampler and the soil sampling recovery rate of the soil sampler for the target tailing fill dam; designing an optimal parameter of the soil sampler according to the relationship function, and selecting the corresponding soil sampler according to the optimal parameter.

Specifically, in this embodiment, because the properties of tailing sand above and below the immersion line of the target tailing fill dam are quite different, the simulation conditions are divided into being above and below the immersion line when simulating the effects of different drilling technologies.

In view of the fact that the tailing layer above the immersion line is drilled without water and mud to protect the wall, dry drilling is used. The detailed simulation results of different drilling technologies are shown in Table 1 below:

| Drilling technologies | Footage per round trip (m) | Core recovery success rate (%) | Core recovery rate (%) | Difficulty degree of drilling operation | Drilling condition |
|---|---|---|---|---|---|
| Reverse circulation drilling | 0.2-0.4 | 50 | 70-80 | easy | stable |
| Impact drilling | 0.1-0.2 | 30 | 70-80 | difficult | stable |
| Auger drilling | 0.8-1.0 | 100 | >90 | easy | stable |

Based on the simulation results of the drilling technologies above the immersion line in Table 1, when collecting tailing sand above the immersion line, an auger drilling bit is selected, and the footage per round trip is 0.8 m to 1.0 m. When taking undisturbed soil, an auger combined drilling tool is used to clean the residual soil at the bottom of the hole from 8 cm to 15 cm, so that the depth and quality of the soil can be guaranteed.

In view of the fact that the tailing sand below the immersion line is saturated, the hole wall collapses, and the hole shrinks seriously. When the drilling depth reaches 2 m to 3 m under the immersion, a casing should be placed into the hole immediately. After the wall is protected with high-quality mud, the detailed simulation results of different drilling technologies are shown in Table 2 below:

| Drilling technologies | Footage per round trip (m) | Core recovery success rate (%) | Core recovery rate (%) | Difficulty degree of drilling operation | Drilling condition |
|---|---|---|---|---|---|
| Pumpless reverse circulation drilling | 1.0-2.0 | 10-20 | 80-90 | easy | stable |
| Impact drilling | 0.8-1.0 | 100 | 40-60 | easy | stable |
| Auger pumpless reverse circulation drilling | 1.0-1.2 | 100 | >90 | difficult | stable |

Based on the simulation results of the drilling technologies below the immersion line in Table 2, when collecting tailing sand below the immersion line, an auger pumpless reverse circulation drilling bit is selected, and the footage per round trip is 1.0 m to 1.2 m. At the same time, in the process of drilling, mud should be sent from the bottom of the hole regularly to wash the hole, and the drilling work should be continued after entering the immersion line, thus ensuring the stability of the hole wall, the high core recovery rate and the high drilling efficiency.

Specifically, in this embodiment, since the deposition time of tailing sand is short, the inter-particle structural strength is poor, and it is difficult to collect Class I undisturbed tailing sand through the soil sampler, the relationship between the area ratio of the soil sampler, the pipe shoe length of the soil sampler, the soil sampling mode of the soil sampler and the soil sampling recovery rate is simulated for the target tailing fill dam. An optimal parameter of the soil sampler is designed according to the relationship, and the corresponding soil sampler is selected according to the optimal parameter.

In view of the relationship between the area ratio of the soil sampler and the pipe shoe length of the soil sampler and the soil sampling recovery rate, the dynamic triaxial soil sampler with thin-walled extension of shoe in which the area ratio is 14.8% and the pipe shoe length is 75 mm, the dynamic triaxial soil sampler with thin-walled extension of shoe in which the area ratio is 14.8% and the pipe shoe length is 160 mm, the static triaxial soil sampler with thin-walled extension of shoe in which the area ratio is 17% and the pipe shoe length is 75 mm, the static triaxial soil sampler with thin-walled extension of shoe in which the area ratio is 17% and the pipe shoe length is 160 mm, and the soil sampling recovery rate of being pressed into the soil with a length of 100 mm to 700 mm are simulated, respectively, so as to the corresponding simulation results. The simulation results are shown in Table 3 below:

| Soil sampler name | Area ratio | Pipe shoe length | Soil sampling recovery rate |
|---|---|---|---|
| Dynamic triaxial soil sampler with extension of shoe thin-walled | 14.8% | 75 | 68-85% |
|  |  | 160 | 59-98% |
| Static triaxial soil sampler with thin-walled extension of shoe | 17% | 75 | 62.5-85% |
|  |  | 160 | 49.5-80% |

From the simulation results, it can be seen that when the length of being pressed into the soil is 100 mm to 700 mm, the area ratio is large, and the soil sampling recovery rate is low, that is, the disturbance to the soil is greater. The larger the area ratio, the thicker the wall thickness of the soil sampler, that is, the thinner the wall thickness of the soil sampler, and the higher the soil sampling recovery rate. Specifically, in this embodiment, the wall thickness of the dynamic triaxial soil sampler with thin-walled extension of shoe is changed to 1.25 mm, and the static triaxial soil sampler with thin-walled extension of shoe is changed to 1.5 mm.

In view of the relationship between the soil sampling mode of the soil sampler and the soil sampling recovery rate, in this embodiment, for the tailing powder clay and the tailing powder sand which have filled for a long time, the standard penetration test blow count reaches 25 to 50, so that it is difficult to sample soil using a static pressure method. Therefore, the soil sampling recovery rate of the soil sampler using the hammer method and the static pressure method is simulated, respectively. In the first test, the soil sampler is hammered with an 8-pound hammer into 40 cm to 60 cm for about 20 to 40 times in the tailing powder sand and the tailing fine sand. For the dynamic triaxial soil sampler with thin-walled extension of shoe/the static triaxial soil sampler with thin-walled extension of shoe which have a large area, the natural density of sampling soil for weighing using the hammering method is 5% to 10% smaller than that of the static pressure method. In the second test, the dynamic triaxial soil sampler with thin-walled extension of shoe/the static triaxial soil sampler with thin-walled extension of shoe which have been modified. When the soil sampler is hammered with a hammer of 63.5 kg into 30 cm to 40 cm for about 3 to 5 times, the soil sampling recovery rate reaches 95%. The physical and mechanical indexes of the tailing sand obtained by the hammering method are basically the same as the soil sampling recovery rate by the static pressure method. The simulation results are shown in Table 4 below:

| Tailing sand | Static triaxial soil sampler with thin-walled extension of shoe | | Dynamic triaxial soil sampler with thin-walled extension of shoe | | Cutting-ring static pressure soil sampler with thin-walled extension of shoe | |
|---|---|---|---|---|---|---|
|  | Pressing length (m) | recovery rate (%) | Pressing length (m) | recovery rate (%) | Pressing length (m) | recovery rate (%) |
| Tailing powder clay | 25 | 100 | 30 | 98.3 | 28 | 98.6 |
|  | 40 | 100 | 30.2 | 99.3 | 28.5 | 98.6 |
|  | 28.5 | 97.5 | 32.4 | 96.9 | 27.2 | 98.5 |
|  | 27.9 | 98.2 | 32.5 | 99 | 26.6 | 99.6 |
|  | 38.2 | 99.7 | 36 | 98.6 | 28 | 97.5 |
|  | 27.5 | 100 |  |  |  |  |
|  | 28.2 | 99.6 |  |  |  |  |

-continued

| | Static triaxial soil sampler with thin-walled extension of shoe | | Dynamic triaxial soil sampler with thin-walled extension of shoe | | Cutting-ring static pressure soil sampler with thin-walled extension of shoe | |
|---|---|---|---|---|---|---|
| Tailing sand | Pressing length (m) | recovery rate (%) | Pressing length (m) | recovery rate (%) | Pressing length (m) | recovery rate (%) |
| Tailing fine sand | 25.6 | 98.4 | 40 | 96.7 | 28.3 | 97.1 |
| | 28.5 | 98.9 | 44 | 95.4 | 34.6 | 95.9 |
| | 32.6 | 84.7 | 50 | 94.4 | 28.6 | 95.8 |
| | 28.2 | 98.9 | 50 | 96 | 29.7 | 97.6 |
| | 28.6 | 96.9 | 39.5 | 98.7 | 30.2 | 95 |
| | 29.6 | 98.6 | | | | |
| | 28.9 | 96.9 | | | | |
| | 29.9 | 100 | | | | |

Therefore, according to the experimental results, the method of sampling soil when the soil sampler is hammered with a hammer of 63.5 kg into 30 cm to 40 cm for about 3 to 5 times is selected.

In this embodiment, according to the relationship between the variables in the above simulation test results and the soil sampling recovery rate, the optimal parameter of the soil sampler is designed in combination with the Technical Standard for Sampling of Undisturbed Soil. Specifically, the wall thickness of the soil sampler is 1.25 mm to 1.5 mm, the internal clearance ratio is 0% to 1.02%, the cutting edge angle is 8 degrees, the external clearance is 0, the area ratio is 9.9% to 15.38%, and the length of the soil sampler is 188 mm to 300 mm. At the same time, the soil sampler for the target tailing fill dam is selected according to the optimal parameters.

S2, tailing sand at different depths of the target tailing fill dam is collected using the drill bit and the soil sampler.

In an alternative embodiment, according to the test results in Table 1 and Table 2, collecting tailing sand at different depths of the target tailing fill dam using the drill bit and the soil sampler comprises the following steps: drilling holes by auger drilling using the drill bit above an immersion line to generate shallow tailing sampling points; collecting tailing sand in the shallow tailing sampling points using the soil sampler; drilling holes by auger pumpless reverse circulation drilling using the drill bit below the immersion line to generate deep tailing sampling points; and collecting tailing sand in the deep tailing sampling points using the soil sampler.

S3, an undisturbed soil sample of the tailing sand is detected.

Figure 2:
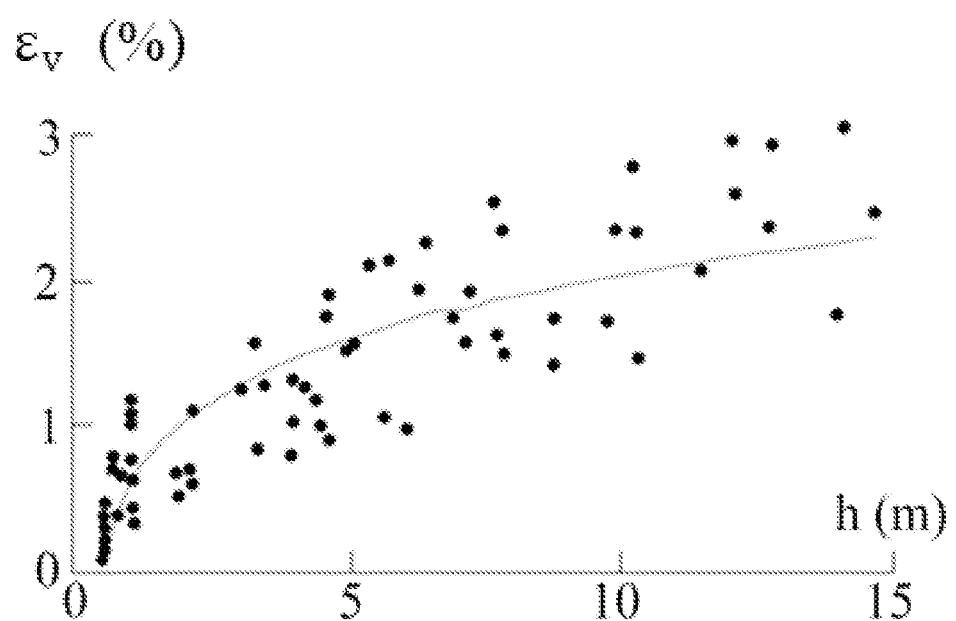
FIG. 2 is a tailing fine sand volumetric strain-depth regression curve according to the present disclosure.
Figure 3:
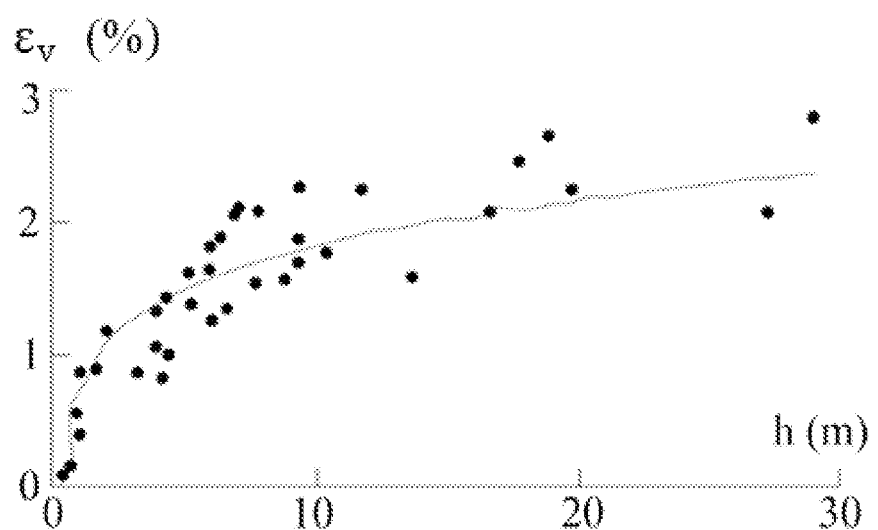
FIG. 3 is a tailing powder sand volumetric strain-depth regression curve according to the present disclosure.
Figure 4:
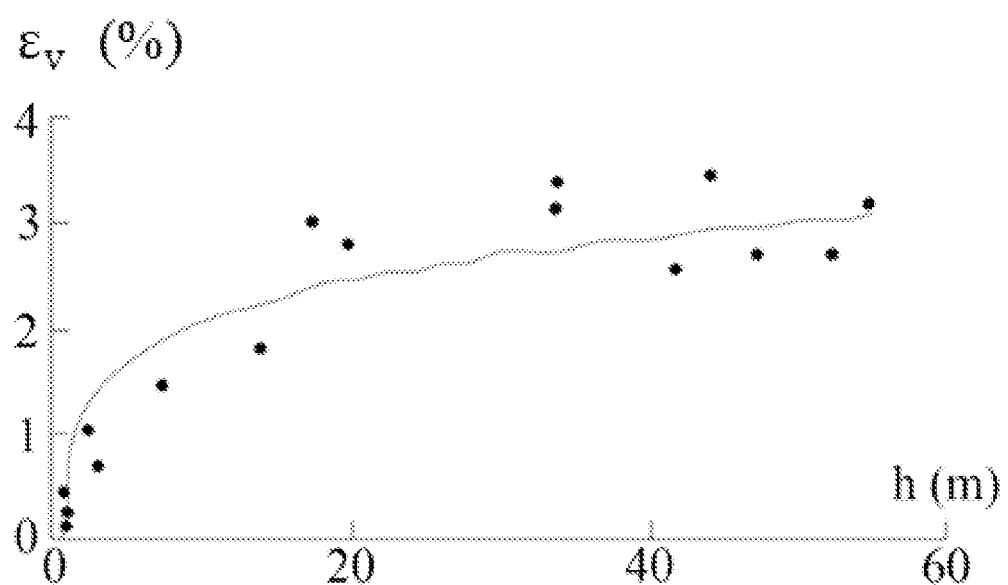
FIG. 4 is a tailing powder soil volumetric strain-depth regression curve according to the present disclosure.

In an alternative embodiment, detecting an undisturbed soil sample of the tailing sand comprises the following steps: presetting the characteristics of the tailing sand according to the structure of the soil sampler, wherein the characteristics comprise a preset volume and a preset surface area of the tailing sand, the preset surface area is related to the inner diameter of the soil sampling pipe of the soil sampler, and the preset volume is related to the inner diameter of the soil sampling pipe and the length of the soil sampling pipe of the soil sampler; using the characteristics to construct an initial undisturbed soil sample judging model, wherein the initial undisturbed soil sample judging model satisfies the following formula:

$$C = \text{average}(S'/S, V'/V),$$

where C represents the degree of the initial undisturbed soil sample of the tailing sand, S' represents the measured surface area of the tailing sand, S represents the preset surface area of the tailing sand, V' represents the measured volume of the tailing sand, and V represents the preset volume of the tailing sand; measuring the tailing sand to obtain a measured volume and a measured surface area. Specifically, the surface area and the volume of the tailing sand sampled by a soil sampler can be obtained by taking pictures of the tailing sand for picture recognition measurement. The undisturbed soil sample of the tailing sand is preliminarily judged according to the measured volume, the measured surface area and the initial undisturbed soil sample judging model. The initial undisturbed soil sample is characterized by the degree of the undisturbed soil sample C, and the value range of C is 0 to 100%. The tailing sand with higher degree of the undisturbed soil sample is more suitable for building subsequent models. A volumetric strain of the tailing sand at different depths is measured. The volumetric strain of the tailing sand is used to fit a tailing sand volumetric strain-depth regression curve equation. In this embodiment, the tailing sand is divided into tailing fine sand, tailing powder sand and tailing powder soil according to the inter-particle adhesion in the particle composition of the tailing sand. The volumetric strain of the tailing sand at different depths is fit, respectively, so as to obtain three regression curve equations, comprising: a tailing fine sand volumetric strain-depth regression curve equation: $\varepsilon_v = 0.5409 \ln h + 0.6636$; a tailing powder sand volumetric strain-depth regression curve equation: $\varepsilon_v = 0.4137 \ln h + 0.8021$; and a tailing powder soil volumetric strain-depth regression curve equation: $\varepsilon_v = 0.5024 \ln h + 0.5284$, where $\varepsilon_v$ represents a volumetric strain value, and h represents the depth of the tailing sand. As shown in FIG. 2 to FIG. 4, FIG. 2 shows the tailing fine sand volumetric strain-depth regression curve, FIG. 3 shows the tailing powder sand volumetric strain-depth regression curve, and FIG. 4 shows the tailing powder soil volumetric strain-depth regression curve. The undisturbed soil sample of the tailing sand is judged again using the tailing sand volumetric strain-depth regression curve equation.

S4, a preset standard is set according to the undisturbed soil sample, and the tailing sand is screened using the preset standard to obtain a tailing sand sample.

In an alternative embodiment, the initial undisturbed soil sample of the tailing sand is detected, and the relationship between the volumetric strain and the depth of the tailing sand is detected again, so that when the preset standard is set, two preset standards: the degree of the undisturbed soil sample C and the volumetric strain value of the tailing sand, are set (when the two preset standards are met, it can be applied suitable for building the subsequent models). (1) In this embodiment, C is in the range of 0 to 100%. The tailing sand sample with higher degree of the undisturbed soil sample is more suitable for building the subsequent models. Specifically, C≥95% is one of the preset standards, and the soil sampler may deform the edge of the collected tailing sand to a certain extent, which will result in errors in the measured volume and the measured surface area in image recognition. However, this will not affect the characterization of the tailing sand sample in the center on the actual physical stress properties. (2) The undisturbed soil sample of the tailing sand is judged again according to the regression curve equation between the depth and the volumetric strain of tailing sand. According to the provisions of Code for investigation of geotechnical engineering (GB50021-2001) (2009 edition), the volumetric strain is proposed as the evaluation standard for evaluating the disturbance degree of soil samples, and the fitting regression curve between the tailing sand with a buried depth of less than 2 meters and the depth is used as an upper boundary curve equation and a lower boundary curve equation. The tailing sand samples corresponding to the volumetric strain value within the range delineated by the two curves corresponding to the upper boundary curve equation and the lower boundary curve equation can be judged as almost undisturbed soil. That is, the tailing sand sample characterized on the regression curve does not exceed the edges of the upper boundary curve and the lower boundary curve, so as to meet the preset standard. Specifically, the upper boundary curve equation, the lower boundary curve equation, and the regression curve equation between the depth and the volumetric strain of the tailing sand are shown in Table 5 below:

| Tailing sand | Upper boundary curve equation | Regression curve equation | Lower boundary curve equation |
|---|---|---|---|
| Tailing fine sand | $\varepsilon_v = 0.7855 \ln h + 0.8013$ | $\varepsilon_v = 0.7855 \ln h + 0.8013$ | $\varepsilon_v = 0.3118 \ln h + 0.5081$ |
| Tailing powder sand | $\varepsilon_v = 0.5177 \ln h + 0.9215$ | $\varepsilon_v = 0.4137 \ln h + 0.8021$ | $\varepsilon_v = 0.3462 \ln h + 0.6675$ |
| Tailing powder soil | $\varepsilon_v = 0.6451 \ln h + 1.0253$ | $\varepsilon_v = 0.5024 \ln h + 0.5284$ | $\varepsilon_v = 0.3788 \ln h + 0.7133$ |

Figure 5:
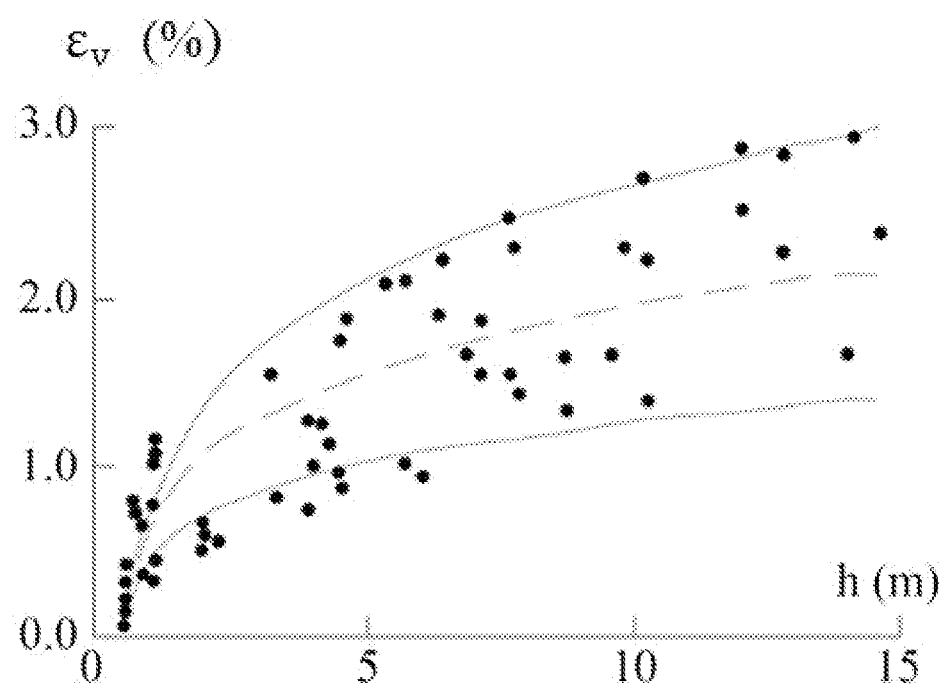
FIG. 5 is a schematic diagram of tailing sand (tailing fine sand) screening according to the present disclosure.
Figure 6:
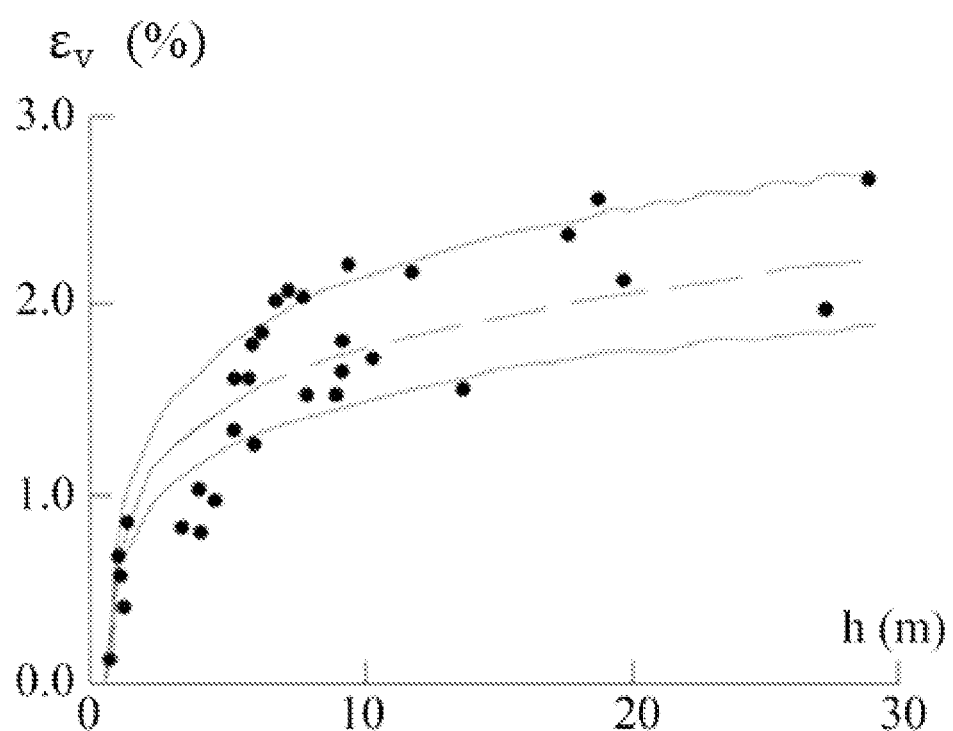
FIG. 6 is a schematic diagram of tailing sand (tailing powder sand) screening according to the present disclosure.
Figure 7:
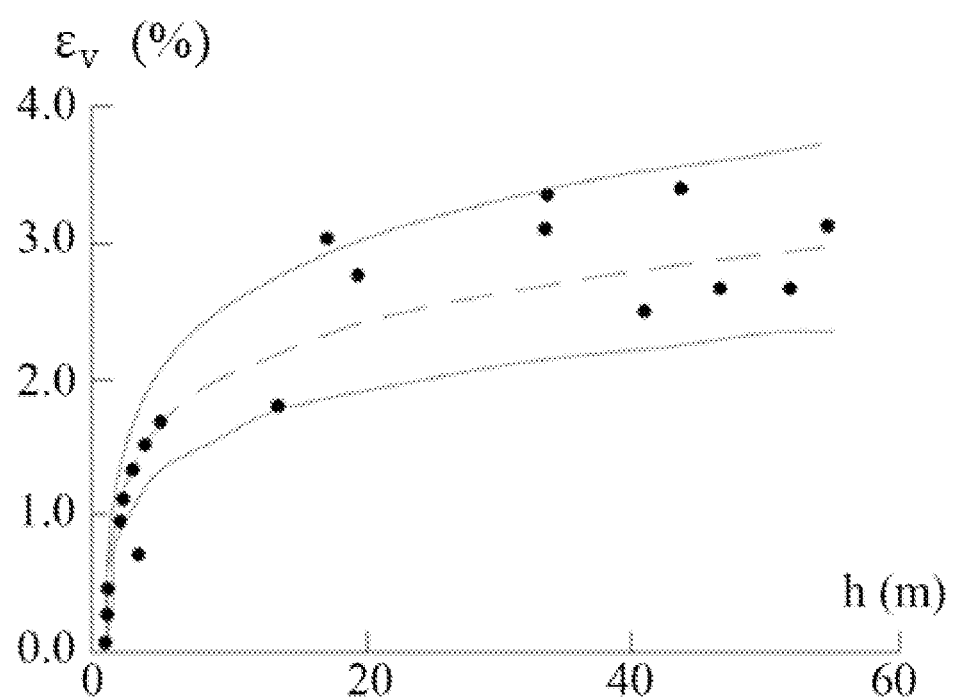
FIG. 7 is a schematic diagram of tailing sand (tailing powder soil) screening according to the present disclosure.

According to Table 5, FIG. 5, FIG. 6 and FIG. 7, FIG. 5 is a schematic diagram of tailing sand (tailing fine sand) screening, FIG. 6 is a schematic diagram of tailing sand (tailing powder sand) screening, and FIG. 7 is a schematic diagram of tailing sand (tailing powder soil) screening. In the figures, the abscissa represents the depth, the ordinate represents the volumetric strain value, and the black dot represents the tailing sand sample. The tailing sand sample characterized by the black dot in the middle of the upper boundary curve equation and the lower boundary curve equation meets the preset standard.

S5, particle composition of the tailing sand sample is detected.

The particle composition comprises the diameter size of particles forming the tailing sand and the number of particles of the tailing sand in different particle diameter ranges. In an alternative embodiment, the particle composition of the tailing sand samples can be specifically divided into a coarse-particle area, a finer-particle area and a fine-particle area according to accumulation and the size of coarse particles and the fine particles, wherein the coarse-particle area mainly comprises tailing soil. The particle composition of the tailing sand samples can be further divided into tailing fine sand and tailing powder sand sub-areas according to the classification principle of sand soil. The finer-particle area mainly comprises tailing powder soil. The fine-particle area mainly comprises tailing powder clay. There may be a very fine-particle sub-area of tailing clay partially in the tailing of the reservoir.

In another alternative embodiment, after the granularity of tailings becomes finer, when the layering and partitioning according to the macroscopic coarse and fine particle sizes do not meet the requirements, the layering and partitioning are selected according to the variation range of the particle size of a certain boundary (such as d50 particle size) according to the deposition law of fill tailings.

S6, the mechanical property of the tailing sand sample is detected.

The mechanical property comprises cohesion, friction strength and shear strength of the tailing sand sample. The cohesion comprises electrostatic attraction between tailing sand particles, Van der Waals force, cementation between particles, valence bond of contact points between particles, and interaction between tailing sand particles, in which the interaction between tailing sand particles, water and an electric system is the most common. The cohesion is the combination of attraction and repulsion between tailing sand particles. The friction strength indicates the degree of sliding and engaging between tailing sand particles, including the sliding friction strength and the engaging friction strength between tailing sand solid particles. Because the tailing sand particles cannot be in plane contact, the staggered arrangement of particles makes the tailing sand particles on the shear plane stagger, rotate and shift, which is accompanied by the volume change of tailing sand, the reorientation of particles and the damage or fracture of particles themselves in the process of mechanical movement. The shear strength is the strength parameter of tailing sand characterized by cohesion and friction strength.

S7, the stability of the target tailing fill dam is evaluated through the particle composition and the mechanical property.

In an alternative embodiment, step S7 comprises the following steps.

① a particle accumulation profile is generated according to the particle composition in combination with a deposition law, wherein the particle accumulation profile comprises an initial dam, a fill dam slope surface, a beach surface, an immersion line, a first particle area, a second particle area, a third particle area and a water storage area.

Figure 8:
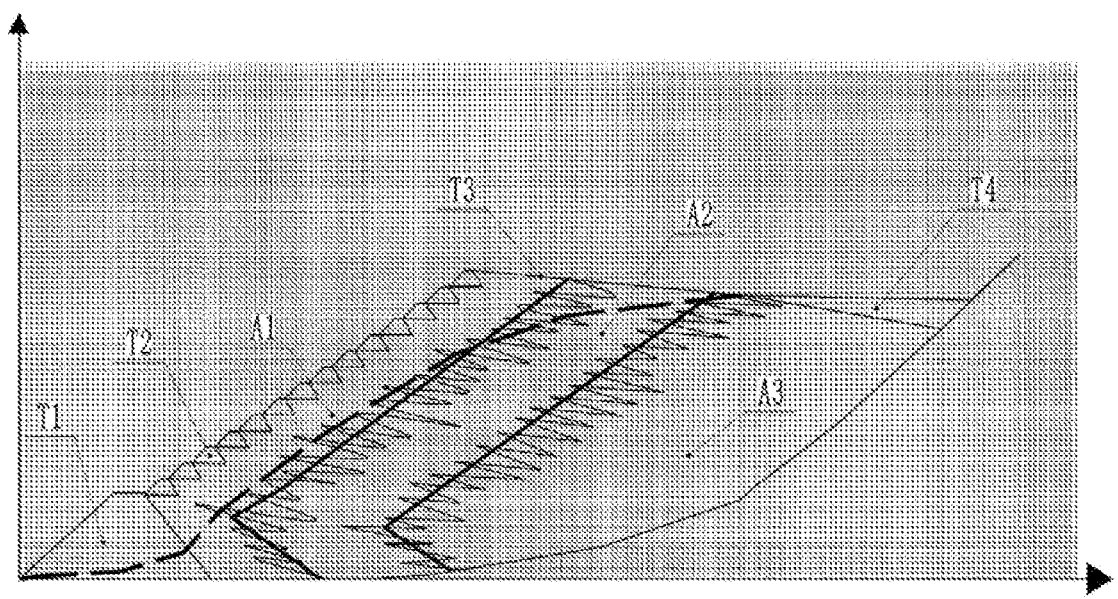
FIG. 8 is a cross-sectional view of particle accumulation according to the present disclosure.

In this embodiment, the deposition law indicates that since in the front section of the dam, the slope of the beach surface is steep, and the hydrodynamic effect is relatively large, only the coarse tailing particles are deposited first, and the finer and fine tailing particles are brought to the distance. In the middle section, when the slope of the beach surface gradually slows down, and the hydrodynamic effect gradually becomes smaller, the finer tailing particles are gradually deposited, while the fine tailing particles are deposited in the tailing section of the reservoir and the underwater section with the smallest hydrodynamic effect. That is to say, the deposition law of the tailing slurry along the beach surface is as follows: coarse-particle tailings are deposited in the front section of the dam, finer-particle tailings are deposited in the middle slope changing (the slope gradually slows down) section, and fine-particle tailings and extremely fine-particle tailings are deposited in the tailing section of the reservoir. According to the deposition law of the tailing slurry along the beach surface, with the increase of deposited tailings, the fill tailings of the upstream tailing fill dam form different particle areas from the dam slope to the reservoir. Generally, according to the particles, the fill tailings can be divided into three areas: coarse-particle area (i.e., a first particle area), a finer-particle area (i.e., a second particle area) and a fine particle area (i.e., a third particle area). Because the partitioning boundaries between different particle sizes are different in the accumulation area below the initial dam crest and in the accumulation area of the fill dam section above the initial dam crest, in the accumulation area below the initial dam crest, the partitioning boundaries are in the same direction as the inner slope of the initial dam, that is, they tend to be in the fill dam. However, the partitioning boundaries in the accumulation area of the fill dam section are in the same direction as the outer slope of the fill dam, that is, they tend to be outside the fill dam. The deposition beach surface on the dam crest of the initial dam is the inflection point of the partitioning boundary in these two accumulation areas, so that the partitioning boundary in these two accumulation areas extend into the dam in the shape of asymmetric sheared edges starting from the inflection point. The height of the initial dam is higher, indicating that the partitioning boundary shaped as a sheared edge is more obvious. As shown in FIG. 8, FIG. 8 is a cross-sectional view of particle accumulation, in which T1 represents the initial dam, T2 represents the fill dam slope surface, T3 represents the beach surface, T4 represents the water storage area, the dotted line represents the immersion line, A1 represents the coarse-particle area, A2 represents the finer-particle area, and A3 represents the fine-particle area. The broken line as a sheared edge is resulted from the inflection point of the partitioning boundary between the two accumulation areas, and the solid black line represents the fitting boundary of the partitioning boundary between the two accumulation areas for calculating the area.

② a consolidation accumulation profile is built according to the mechanical property in combination with a tailing discharge mode, wherein the consolidation accumulation profile comprises an initial dam, a fill dam slope surface, a beach surface, an immersion line, a first consolidation area, a second consolidation area, a third consolidation area and a water storage area;

Because the partitioning according to the particle size fails to reflect the differences of consolidation forms and physical and mechanical properties of fill tailings, there is one-sidedness, which will lead to the lack of pertinence in the stability analysis of the upstream tailing fill dam. The consolidation properties of fill tailings should also be considered. In this embodiment, the tailing discharge mode of the target tailing fill dam is a time-divided and partitioning manually-controlled discharge mode. The time for discharging tailings each time is short, generally less than 3 hours. When the tailing discharge process is combined with the mechanical property, it can be seen according to analysis that for the fill tailings in the tailing fill dam, the fill tailings in the shallow layer of the dry beach surface above the immersion line are in a frequently alternating unsaturated and saturated environment; the fill tailings on the slope section of the fill dam above the immersion line are in a relatively stable unsaturated environment; and the fill tailings below the immersion line are in a relatively stable saturated environment. That is, the fill tailings above the immersion line have leaching consolidation and chemical consolidation effects besides the self-weight consolidation effect, while the fill tailings below the immersion line mainly have the self-weight consolidation effect. According to the tailing discharge mode, the vertical line drawn from the tailing fill dam crest crosses the immersion line. Taking this vertical line as the boundary and combined with the beach surface, the slope surface of the fill dam, the initial dam and the immersion line, the fill tailings in the tailing fill dam can be divided into three different water environment areas, that is, three different consolidation areas. Partitioning is described as follows.

A first consolidation area: the area surrounded by the vertical line at the dam crest, the dry beach surface in the reservoir area and the immersion line is divided into the first consolidation area. The first consolidation area is the area where the leaching consolidation effect is completed and the chemical consolidation effect is strengthened. Generally, the scope of the first consolidation area is relatively fixed. With the gradual heightening of the tailing fill dam, the whole first consolidation area moves upstream accordingly. The first consolidation area is a frequent alternating unsaturated and saturated area.

A second consolidation area: the area surrounded by the vertical line at the dam crest, the slope surface of the dam, the slope surface line in the initial dam and the immersion line is the second consolidation area. The second consolidation area is the area where the leaching consolidation effect and the chemical consolidation effect are stable. The second consolidation area is gradually transformed from the first consolidation area. With the gradual heightening of the tailing fill dam, the second consolidation area expands upstream accordingly. The second consolidation area is an unsaturated area.

A third consolidation area: the tailing fill area below the immersion line belongs to the third consolidation area. The third consolidation area is the area of the self-weight consolidation effect. A chemical consolidation weakening zone will be formed near the immersion line due to the fluctuation of the water level. With the gradual heightening of tailing fill dam, the third consolidation area also expands upstream accordingly. The third consolidation area is a saturated area.

Figure 9:
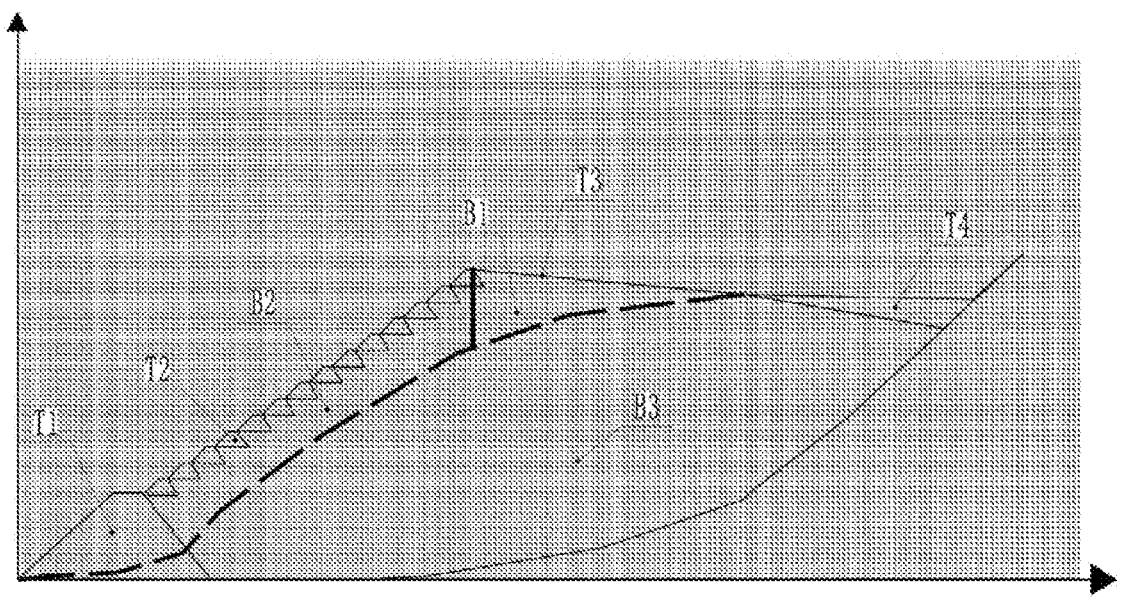
FIG. 9 is a cross-sectional view of consolidation accumulation according to the present disclosure.

As shown in FIG. 9, FIG. 9 is a cross-sectional view of consolidation accumulation, in which T1 represents the initial dam, T2 represents the slope surface of the fill dam, T3 represents the beach surface, T4 represents the water storage area, the dotted line represents the immersion line, B1 represents the first consolidation area, B2 represents the second consolidation area, and B3 represents the third consolidation area (the initial dam, the slope surface of the fill dam, the beach surface and the immersion line in the consolidation accumulation model and the tailing fill model are in the same position, which can be mapped through field exploration).

③ first parameter information of a first particle area, a second particle area and a third particle area in the particle accumulation profile is extracted, wherein the first parameter information comprises particle distribution area size, particle component and particle distribution position.

④ second parameter information of the first consolidation area, the second consolidation area and the third consolidation area in the consolidation accumulation profile is extracted, wherein the second parameter information comprises the mechanical property of consolidation, the area size of the same consolidation mode and the distribution position of the same consolidation mode.

⑤ a stability evaluation function is constructed by combining the first parameter information with the second parameter information.

In an alternative embodiment, the stability evaluation function satisfies the following formula:

$$E = \begin{cases} 1 - \dfrac{S_a/S_B}{S_b/S_B} - \dfrac{S_b}{S_B} \cdot e^{-\frac{f-\mu}{\tau_f - \mu}}, & (\alpha K_{Aa}, \beta K_{Bb}, \gamma K_{Cc})_{max} = \alpha K_{Aa} \\ 1 - \dfrac{S_a}{S_A} \cdot \left( \dfrac{f-\mu}{\tau_f - \mu} + \omega \right), & (\alpha K_{Aa}, \beta K_{Bb}, \gamma K_{Cc})_{max} = \beta K_{Bb} \\ \dfrac{S_b/S_C}{S_c/S_C} + \dfrac{S_c}{S_C} \cdot e^{-1/\omega}, & (\alpha K_{Aa}, \beta K_{Bb}, \gamma K_{Cc})_{max} = \gamma K_{Cc} \end{cases}$$

where $E \in (0,1)$, E represents the stability of the target tailing fill dam, $S_a$ represents the area of the first particle area, $S_b$ represents the area of the second particle area, $S_c$ represents the area of the third particle area, $S_A$ represents the area of the first consolidation area, $S_B$ represents the area of the second consolidation area, $S_C$ represents the area of the third consolidation area, f represents the cohesion of the tailing sand sample, $\tau_f$ represents the shear strength of the tailing sand sample, $\mu$ represents the stress correction of the tailing sand sample, $\omega$ represents the friction strength coefficient of the tailing sand sample, $K_{Aa}$ represents the proportion of the area of the first particle area in the area of the first consolidation area, α represents the normalization coefficient of $K_{Aa}$, $K_{Bb}$ represents the proportion of the area of the second particle area in the area of the second consolidation area, β represents the normalization coefficient of $K_{Bb}$, $K_{Cc}$ represents the proportion of the area of the third particle area in the area of the third consolidation area, and γ represents the normalization coefficient of $K_{Cc}$. Specifically, in this embodiment, α=1.2085, β=0.7562, and γ=1.0661. According to the present disclosure, the stability of the target tailing fill dam is quantified by the stability evaluation function, so that the stability of the target tailing fill dam can be visually presented by numbers.

⑥ the stability of the target tailing fill dam is evaluated using the stability evaluation function.

In an alternative embodiment, step S76 uses the stability evaluation function to obtain the stability value of the target tailing fill dam. That is, based on the consolidation accumulation model, the area ratios of the first particle area, the second particle area and the third particle area corresponding to the same positions of the first consolidation area, the second consolidation area and the third consolidation area in the particle accumulation model are calculated, respectively, and the stability value of the target tailing fill dam is obtained according to the particle differentiation rules and stress analysis of the first particle area, the second particle area and the third particle area. Specifically, $(\alpha K_{Aa} \beta K_{Bb} \gamma K_{Cc})_{max} = \alpha K_{Aa}$, that is, in the first consolidation area, the consolidation effect is strong, and $$E = 1 - \frac{\frac{s_a}{s_B}}{\frac{s_b}{s_B}} - \frac{s_b}{s_B} \cdot e^{-\frac{f-\mu}{\tau_f - \mu}} = 0.724,$$

in which $$\frac{s_b}{s_B} = 0.64 > \frac{s_a}{s_B} = 0.31.$$

That is, the area ratio of the finer-particle area is large. At this time, the leaching consolidation effect is strong in the first consolidation area (the leaching consolidation effect is mainly related to the capillary suction, especially for the tailing powder sand and the tailing powder soil in the finer-particle area). That is, the compactness of the tailing sand can be increased in a short time. That is, the tailing sand filled in the shallow part of the target tailing fill dam can have high mechanical strength in a short time through the leaching consolidation effect. The stability of the target tailing fill dam is high at this time.

According to the present disclosure, through steps S1 to S7, a drill bit and a soil sampler which are appropriate are selected for the target tailing fill dam to collect the actual tailing sand, so that the sampling resistance resulted from the difference of particle shapes and particle compositions of different tailing fill dams is weakened. Meanwhile, the accuracy of subsequent analysis using the tailing sand data is ensured by detecting an undisturbed soil sample of the collected tailing sand. The stability of the target tailing fill dam corresponding to the stability evaluation function constructed by the actually collected parameters is evaluated, so that the evaluation quality is ensured. Through the present disclosure, the actual state and the stability state of the upstream tailing fill dam can be mastered, which provides a basis for correctly managing the upstream tailing fill dam, handling tailing accidents, maintaining the upstream tailing fill dam and the like. In addition, the present disclosure can also find the abnormal signs of the upstream tailing fill dam in time, and analyze the reasons according to the relevant data, so as to take timely measures to prevent the upstream tailing fill dam from accidents.

In another embodiment, the method for survey and stability evaluation of the upstream tailing fill dam of the present disclosure further comprises the following steps:

simulating a frost heaving condition of the tailing sand sample at different depths at different temperatures;

measuring water content of the tailing sand sample;

obtaining preservation temperature by combining the water content with the frost heaving condition; and setting the preservation temperature to preserve the tailing sand sample.

Due to the limitation of field conditions, hundreds of undisturbed tailing soil samples need to be transported to an indoor laboratory for experiment. It is a difficult problem to keep the undisturbed samples in long-distance transportation because of the low strength of the intergranular structure of the tailing sand. In the present disclosure, tailing sand samples are preserved through steps S11 to S14, specifically, by simulating the frost heaving condition of tailing sand samples at different depths at different temperatures. Specifically, the tailing sand samples sampled from the test borehole using a soil sampler are sealed together with the soil sampler and placed in a refrigerator. The temperatures of different grades are measured by a refrigerator thermometer as −12° C., −18° C., −20° C. and −24° C., respectively, and temperatures of the four grades are used for freezing simulation. After 20 days of continuous observation, the simulation results show that the tailing fine sand and the tailing powder sand with low water content (<40%) do not find frost heaving during the observation from 5 days to 6 days, but the surface of the tailing sand sample is frosted; after freezing at −12° C. for 2 hours, the tailing powder soil and the tailing powder clay with water content of about 40% find tiny frost spots on the surface of the tailing sand sample. The inside of the cut tailing sand sample is similar to that of the unfrozen tailing sand sample. No frost heaving is found after freezing for 3 to 4 hours, but frost heaving is found after freezing at −24° C. for 4 hours. Although the tailing powder sand finds no frost heaving after freezing at −24° C. for 19 hours, the center of the sample has frozen into a hard block. At the same time, the water content is an important influence factor of freezing on tailing sand samples. The water content of the tailing fine sand and the tailing powder sand is 2% to 8%, which is less than their initial frost heaving water content. No frost heaving is found from frozen tailing sand samples. However, the tailing powder soil and the tailing powder clay with high water content (>8%) find frost heaving after freezing for a few hours. The lower the temperature, the shorter the frost heaving time. In a short time (2 hours to 3 hours), only a slightly hard "shell" is formed at the temperature of −12° C., which is beneficial to indoor sample preparation. Therefore, the tailing fine sand and the tailing powder sand with low water content can be preserved and transported by a freezing method, and the freezing temperature is about −12° C. The tailing powder sand and the tailing powder clay with large water content can only be preserved with a humidifier to prevent the loss of water content, and cannot be transported by the freezing method either. During transportation, there should be a moisturizing and shock-proof device, which can be frozen at −12° C. for 1 hour to 2 hours in the laboratory, and then thawed at the natural temperature for 10 to 30 minutes before use.

Figure 10:
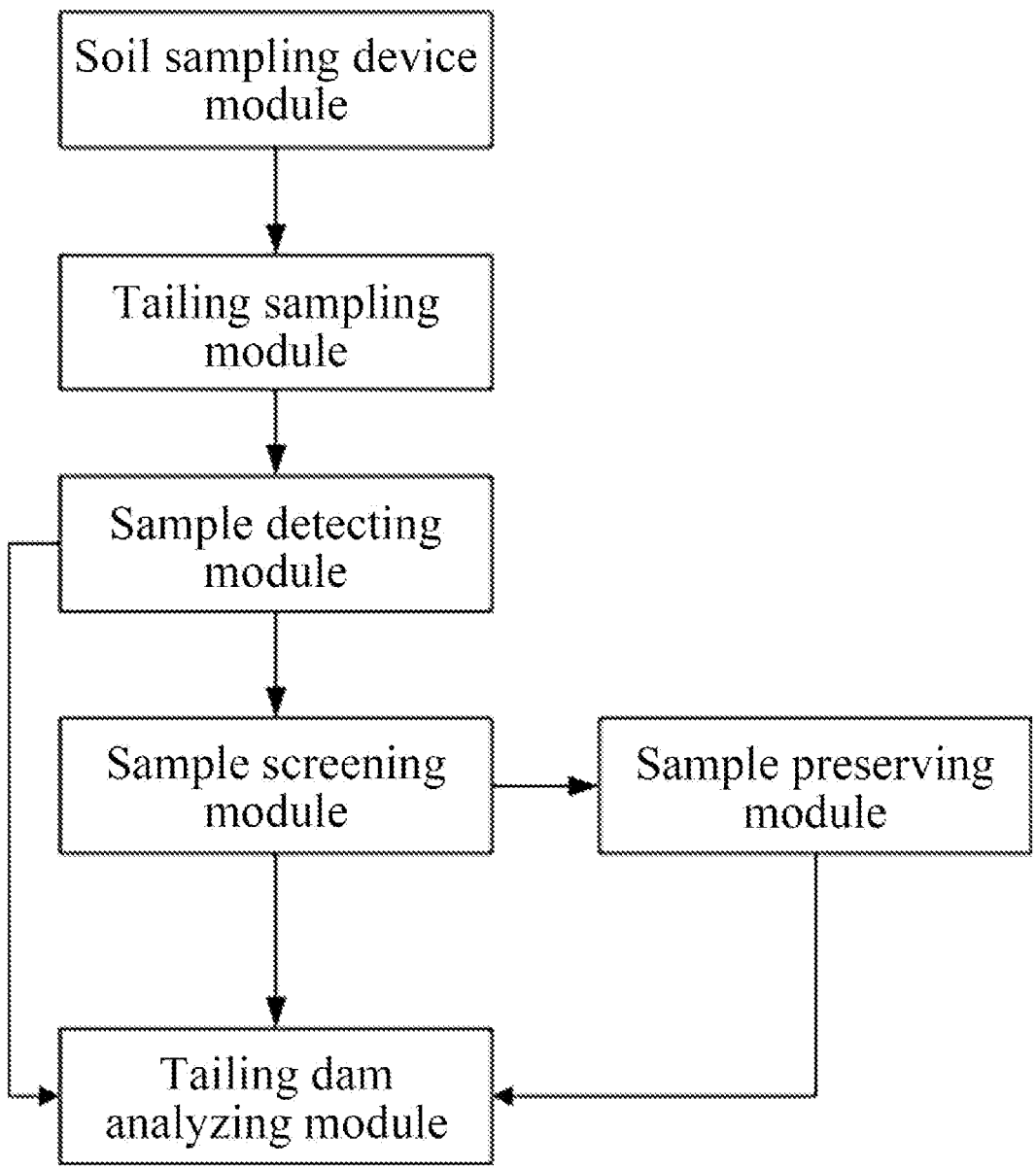
FIG. 10 is a structural diagram of a system for survey and stability evaluation of an upstream tailing fill dam according to the present disclosure.

In one embodiment, as shown in FIG. 10, the present disclosure further provides a system for survey and stability evaluation of an upstream tailing fill dam, wherein the system for survey and stability evaluation of the upstream tailing fill dam is suitable for the method for survey and stability evaluation of the upstream tailing fill dam described in the first aspect, comprising: a soil sampling device module, which is configured to select a drill bit and a soil sampler for a target tailing fill dam; a tailing sampling module, which is configured to collect tailing sand at different depths of the target tailing fill dam using the drill bit and the soil sampler; a sample detecting module, which is configured to detect an undisturbed soil sample, particle composition and mechanical property of the tailing sand; a sample screening module, which is configured to set a preset standard according to the undisturbed soil sample, and screen the tailing sand using the preset standard to obtain a tailing sand sample; a sample preserving module, which is configured to preserve the tailing sand sample; a tailing dam analyzing module, which is configured to evaluate the stability of the target tailing fill dam through the particle composition and the mechanical property. Through the cooperation of a plurality of functional modules, the present disclosure realizes the stable implementation of the method for survey and stability evaluation of the upstream tailing fill dam, has strong robustness, and improves the practical benefit and commercial value of the present disclosure. At the same time, the present disclosure further provides tools for correctly managing the upstream tailing fill dam, handling tailing accidents, maintaining the upstream tailing fill dam and the like.

In an alternative embodiment, the soil sampling device module selects the following deep drilling sampling device for the high tailing dam. The deep drilling sampling device for the high tailing dam comprises a drilling component, a sand lifting component and a driving component. The drilling component comprises a drill bit, a hollow drill rod and a sampling cylinder. One end of the sampling cylinder is fixedly connected with the drill bit, and the other end of the sampling cylinder is fixedly connected with the hollow drill rod. The drill bit is provided with a circular through hole along the center line direction. The axes of the drill bit, the hollow drill rod and the sampling cylinder are on the same straight line. The drill bit, the hollow drill rod and the sampling cylinder are communicated internally. The sand lifting component comprises a lifting screw. The lifting screw is provided inside the hollow drill rod. The lifting screw is rotatably connected with the hollow drill rod. The driving component is configured to drive the hollow drill rod and the screw to rotate. The rotating directions of the hollow drill rod and the lifting screw are opposite to each other. The deep drilling sampling device for the high tailing dam drives the drilling component and the sand lifting component to rotate in opposite directions through the driving component. The drilling component performs rotary drilling on the tailing dam. The drill bit performs rotary cutting on the tailing sand during drilling. The tailing sand enters the sampling cylinder along the central through hole of the drill bit. After the sand in the sampling cylinder is filled, the sand enters the hollow drill rod. The sand in the hollow drill rod is lifted to the ground along the hollow drill rod by the rotation of the lifting screw. The newly drilled sand sample is kept in the sampling cylinder at any time. In the whole sampling process, drilling for sampling is required for only one time. The drilling process and the sampling process are combined, so that the problem that the wall of a drilled hole is easy to collapse is effectively prevented.

Figure 11:
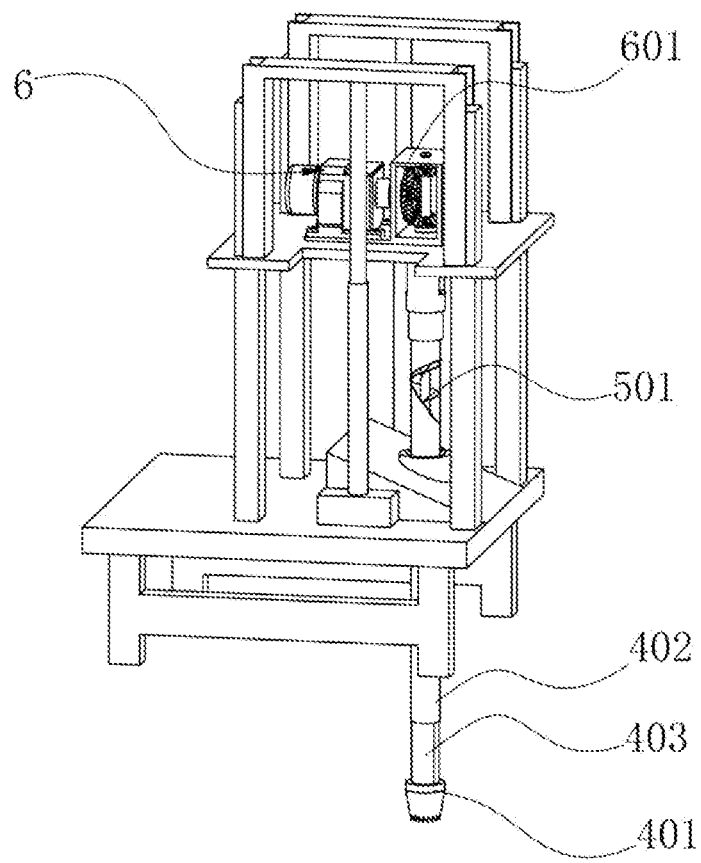
FIG. 11 is a schematic structural diagram of a deep drilling sampling device for a high tailing dam according to the present disclosure.

In this embodiment, as shown in FIG. 11, the drilling component comprises a drill bit 401, a hollow drill rod 402 and a sampling cylinder 403. One end of the sampling cylinder 403 is fixedly connected with the drill bit 401, and the other end of the sampling cylinder 403 is fixedly connected with the hollow drill rod 402. The drill bit is provided with a circular through hole along the center line direction. The axes of the drill bit 401, the hollow drill rod 402 and the sampling cylinder 403 are on the same straight line. The drill bit 401, the hollow drill rod 402 and the sampling cylinder 403 are communicated internally. The sand lifting component comprises a lifting screw 501. The lifting screw 501 is provided inside the hollow drill rod 402. The driving component 6 is configured to drive the hollow drill rod 402 and the lifting screw 501 to rotate. The rotating directions of the hollow drill rod 402 and the lifting screw 501 are opposite to each other. The drilling component and the sand lifting component are driven to rotate in opposite directions through the driving component 6. The drilling component performs rotary drilling on the tailing dam. The drill bit 401 performs rotary cutting on the tailing sand during drilling. The tailing sand enters the sampling cylinder 403 along the central through hole of the drill bit 401. After the sand in the sampling cylinder 403 is filled, the sand enters the hollow drill rod 402. The sand in the hollow drill rod 402 is lifted to the ground along the hollow drill rod 402 by the rotation of the lifting screw 501. The newly drilled sand sample is kept in the sampling cylinder 403 at any time. In the whole sampling process, drilling for sampling is required for only one time. The drilling process and the sampling process are combined, so that the problem that the wall of a drilled hole is easy to collapse is effectively prevented.

Finally, it should be explained that the above embodiments are only used to illustrate the technical scheme of the present disclosure, rather than limit the technical scheme. Although the present disclosure has been described in detail with reference to the foregoing embodiments, it should be understood by those skilled in the art that the technical scheme described in the foregoing embodiments can still be modified, or some or all of the technical features can be replaced equivalently. However, these modifications or replacements do not make the essence of the corresponding technical scheme deviate from the scope of the technical scheme of various embodiments of the present disclosure, which should be included in the scope of the claims and the specification of the present disclosure.

What is claimed is:

1. A method for survey and stability evaluation of an upstream tailing fill dam, comprising the following steps:
   selecting a drill bit and a soil sampler for a target tailing fill dam;
   collecting tailing sand at different depths of the target tailing fill dam using the drill bit and the soil sampler;
   detecting an undisturbed soil sample of the tailing sand;
   setting a preset standard according to the undisturbed soil sample, and screening the tailing sand using the preset standard to obtain a tailing sand sample;
   detecting particle composition of the tailing sand sample, wherein the particle composition comprises the diameter size of particles forming the tailing sand and the number of particles of the tailing sand in different particle diameter ranges;

detecting the mechanical property of the tailing sand sample, wherein the mechanical property comprises cohesion, friction strength and shear strength of the tailing sand sample;

evaluating the stability of the target tailing fill dam through the particle composition and the mechanical property;

wherein detecting an undisturbed soil sample of the tailing sand comprises the following steps:

presetting the characteristics of the tailing sand according to the structure of the soil sampler, wherein the characteristics comprise a preset volume and a preset surface area of the tailing sand;

using the characteristics to construct an initial undisturbed soil sample judging model;

measuring the tailing sand to obtain a measured volume and a measured surface area;

preliminarily judging the undisturbed soil sample of the tailing sand according to the measured volume, the measured surface area and the initial undisturbed soil sample judging model;

measuring a volumetric strain of the tailing sand at different depths;

using the volumetric strain of the tailing sand to fit a tailing sand volumetric strain-depth regression curve equation;

judging the undisturbed soil sample of the tailing sand again using the tailing sand volumetric strain-depth regression curve equation;

in which the initial undisturbed soil sample judging model satisfies the following formula:

$$C = \mathrm{average}(S'/S, V'/V),$$

where C represents the degree of the initial undisturbed soil sample of the tailing sand, S' represents the measured surface area of the tailing sand, S represents the preset surface area of the tailing sand, V' represents the measured volume of the tailing sand, and V represents the preset volume of the tailing sand.

2. The method for survey and stability evaluation of the upstream tailing fill dam according to claim 1, further comprising the following steps:

simulating a frost heaving condition of the tailing sand sample at different depths at different temperatures;

measuring water content of the tailing sand sample;

obtaining preservation temperature by combining the water content with the frost heaving condition;

setting the preservation temperature to preserve the tailing sand sample.

3. A system for survey and stability evaluation of an upstream tailing fill dam, wherein the system for survey and stability evaluation of the upstream tailing fill dam is suitable for the method for survey and stability evaluation of the upstream tailing fill dam according to claim 2, comprising:

a soil sampling device module, which is configured to select a drill bit and a soil sampler for a target tailing fill dam;

a tailing sampling module, which is configured to collect tailing sand at different depths of the target tailing fill dam using the drill bit and the soil sampler;

a sample detecting module, which is configured to detect an undisturbed soil sample, particle composition and mechanical property of the tailing sand;

a sample screening module, which is configured to set a preset standard according to the undisturbed soil sample, and screen the tailing sand using the preset standard to obtain a tailing sand sample;

a sample preserving module, which is configured to preserve the tailing sand sample;

a tailing dam analyzing module, which is configured to evaluate the stability of the target tailing fill dam through the particle composition and the mechanical property.

4. The method for survey and stability evaluation of the upstream tailing fill dam according to claim 1, wherein selecting the drill bit and the soil sampler for the target tailing fill dam comprises the following steps:

simulating a core recovery success rate, a core recovery rate, a difficulty degree of drilling operation and a drilling condition of different drilling technologies for the target tailing fill dam, wherein the different drilling technologies comprise impact drilling, reverse circulation drilling, pumpless reverse circulation drilling, auger drilling and auger pumpless reverse circulation drilling;

selecting an optimal drilling mode according to the core recovery success rate, the core recovery rate, the difficulty degree of drilling operation and the drilling condition, and selecting a corresponding drill bit according to the optimal drilling mode;

simulating a relationship function between a soil sampling area of the soil sampler, a soil sampling length of the soil sampler, a soil sampling mode of the soil sampler and a soil sampling recovery rate of the soil sampler for the target tailing fill dam;

designing an optimal parameter of the soil sampler according to the relationship function, and selecting the corresponding soil sampler according to the optimal parameter.

5. The method for survey and stability evaluation of the upstream tailing fill dam according to claim 4, wherein collecting tailing sand at different depths of the target tailing fill dam using the drill bit and the soil sampler comprises the following steps:

drilling holes by auger drilling using the drill bit above an immersion line to generate shallow tailing sampling points;

collecting tailing sand in the shallow tailing sampling points using the soil sampler;

drilling holes by auger pumpless reverse circulation drilling using the drill bit below the immersion line to generate deep tailing sampling points;

collecting tailing sand in the deep tailing sampling points using the soil sampler.

6. A system for survey and stability evaluation of an upstream tailing fill dam, wherein the system for survey and stability evaluation of the upstream tailing fill dam is suitable for the method for survey and stability evaluation of the upstream tailing fill dam according to claim 5, comprising:

a soil sampling device module, which is configured to select a drill bit and a soil sampler for a target tailing fill dam;

a tailing sampling module, which is configured to collect tailing sand at different depths of the target tailing fill dam using the drill bit and the soil sampler;

a sample detecting module, which is configured to detect an undisturbed soil sample, particle composition and mechanical property of the tailing sand;

a sample screening module, which is configured to set a preset standard according to the undisturbed soil sample, and screen the tailing sand using the preset standard to obtain a tailing sand sample;

a sample preserving module, which is configured to preserve the tailing sand sample;

a tailing dam analyzing module, which is configured to evaluate the stability of the target tailing fill dam through the particle composition and the mechanical property.

7. A system for survey and stability evaluation of an upstream tailing fill dam, wherein the system for survey and stability evaluation of the upstream tailing fill dam is suitable for the method for survey and stability evaluation of the upstream tailing fill dam according to claim 4, comprising:
   a soil sampling device module, which is configured to select a drill bit and a soil sampler for a target tailing fill dam;
   a tailing sampling module, which is configured to collect tailing sand at different depths of the target tailing fill dam using the drill bit and the soil sampler;
   a sample detecting module, which is configured to detect an undisturbed soil sample, particle composition and mechanical property of the tailing sand;
   a sample screening module, which is configured to set a preset standard according to the undisturbed soil sample, and screen the tailing sand using the preset standard to obtain a tailing sand sample;
   a sample preserving module, which is configured to preserve the tailing sand sample;
   a tailing dam analyzing module, which is configured to evaluate the stability of the target tailing fill dam through the particle composition and the mechanical property.

8. The method for survey and stability evaluation of the upstream tailing fill dam according to claim 1, wherein the tailing sand volumetric strain-depth regression curve equation comprises:
   a tailing fine sand volumetric strain-depth regression curve equation: $\varepsilon_v = 0.5409 \ln h + 0.6636$;
   a tailing powder sand volumetric strain-depth regression curve equation: $\varepsilon_v = 0.4137 \ln h + 0.8021$;
   a tailing powder soil volumetric strain-depth regression curve equation: $\varepsilon_v = 0.5024 \ln h + 0.5284$;
   where $\varepsilon_v$ represents a volumetric strain value, and h represents the depth of the tailing sand.

9. A system for survey and stability evaluation of an upstream tailing fill dam, wherein the system for survey and stability evaluation of the upstream tailing fill dam is suitable for the method for survey and stability evaluation of the upstream tailing fill dam according to claim 8, comprising:
   a soil sampling device module, which is configured to select a drill bit and a soil sampler for a target tailing fill dam;
   a tailing sampling module, which is configured to collect tailing sand at different depths of the target tailing fill dam using the drill bit and the soil sampler;
   a sample detecting module, which is configured to detect an undisturbed soil sample, particle composition and mechanical property of the tailing sand;
   a sample screening module, which is configured to set a preset standard according to the undisturbed soil sample, and screen the tailing sand using the preset standard to obtain a tailing sand sample;
   a sample preserving module, which is configured to preserve the tailing sand sample;
   a tailing dam analyzing module, which is configured to evaluate the stability of the target tailing fill dam through the particle composition and the mechanical property.

10. The method for survey and stability evaluation of the upstream tailing fill dam according to claim 1, wherein evaluating the stability of the target tailing fill dam through the particle composition and the mechanical property comprises the following steps:
   generating a particle accumulation profile according to the particle composition in combination with a deposition law, wherein the particle accumulation profile comprises an initial dam, a fill dam slope surface, a beach surface, an immersion line, a first particle area, a second particle area, a third particle area and a water storage area;
   building a consolidation accumulation profile according to the mechanical property in combination with a tailing discharge mode, wherein the consolidation accumulation profile comprises an initial dam, a fill dam slope surface, a beach surface, an immersion line, a first consolidation area, a second consolidation area, a third consolidation area and a water storage area;
   extracting first parameter information of a first particle area, a second particle area and a third particle area in the particle accumulation profile, wherein the first parameter information comprises particle distribution area size, particle component and particle distribution position;
   extracting second parameter information of the first consolidation area, the second consolidation area and the third consolidation area in the consolidation accumulation profile, wherein the second parameter information comprises the mechanical property of consolidation, the area size of the same consolidation mode and the distribution position of the same consolidation mode;
   constructing a stability evaluation function by combining the first parameter information with the second parameter information;
   evaluating the stability of the target tailing fill dam using the stability evaluation function;
   wherein the stability evaluation function satisfies the following formula:

$$E = \begin{cases} 1 - \dfrac{S_a/S_B}{S_b/S_B} - \dfrac{S_b}{S_B} \cdot e^{-\frac{f-\mu}{\tau_f-\mu}}, & (\alpha K_{Aa}, \beta K_{Bb}, \gamma K_{Cc})_{max} = \alpha K_{Aa} \\ 1 - \dfrac{S_a}{S_A} \cdot \left( \dfrac{f-\mu}{\tau_f-\mu} + \omega \right), & (\alpha K_{Aa}, \beta K_{Bb}, \gamma K_{Cc})_{max} = \beta K_{Bb} \\ \dfrac{S_b/S_C}{S_c/S_C} + \dfrac{S_c}{S_C} \cdot e^{-1/\omega}, & (\alpha K_{Aa}, \beta K_{Bb}, \gamma K_{Cc})_{max} = \gamma K_{Cc} \end{cases}$$

where $E \in (0,1)$, E represents the stability of the target tailing fill dam, $S_a$ represents the area of the first particle area, $S_b$ represents the area of the second particle area, $S_c$ represents the area of the third particle area, $S_A$ represents the area of the first consolidation area, $S_B$ represents the area of the second consolidation area, $S_C$ represents the area of the third consolidation area, f represents the cohesion of the tailing sand sample, $\tau_f$ represents the shear strength of the tailing sand sample, $\mu$ represents the stress correction of the tailing sand sample, $\omega$ represents the friction strength coefficient of the tailing sand sample, $K_{Aa}$ represents the proportion of the area of the first particle area in the area of the first consolidation area, $\alpha$ represents the normalization coefficient of $K_{Aa}$, $K_{Bb}$ represents the proportion of the area of the second particle area in the area of the second consolidation area, $\beta$ represents the normalization coefficient of $K_{Bb}$, $K_{Cc}$ represents the proportion of the area of the third particle area in the area of the third consolidation area, and γ represents the normalization coefficient of $K_{Cc}$.

11. A system for survey and stability evaluation of an upstream tailing fill dam, wherein the system for survey and stability evaluation of the upstream tailing fill dam is suitable for the method for survey and stability evaluation of the upstream tailing fill dam according to claim 10, comprising:
- a soil sampling device module, which is configured to select a drill bit and a soil sampler for a target tailing fill dam;
- a tailing sampling module, which is configured to collect tailing sand at different depths of the target tailing fill dam using the drill bit and the soil sampler;
- a sample detecting module, which is configured to detect an undisturbed soil sample, particle composition and mechanical property of the tailing sand;
- a sample screening module, which is configured to set a preset standard according to the undisturbed soil sample, and screen the tailing sand using the preset standard to obtain a tailing sand sample;
- a sample preserving module, which is configured to preserve the tailing sand sample;
- a tailing dam analyzing module, which is configured to evaluate the stability of the target tailing fill dam through the particle composition and the mechanical property.

12. A system for survey and stability evaluation of an upstream tailing fill dam, wherein the system for survey and stability evaluation of the upstream tailing fill dam is suitable for the method for survey and stability evaluation of the upstream tailing fill dam according to claim 1, comprising:
- a soil sampling device module, which is configured to select a drill bit and a soil sampler for a target tailing fill dam;
- a tailing sampling module, which is configured to collect tailing sand at different depths of the target tailing fill dam using the drill bit and the soil sampler;
- a sample detecting module, which is configured to detect an undisturbed soil sample, particle composition and mechanical property of the tailing sand;
- a sample screening module, which is configured to set a preset standard according to the undisturbed soil sample, and screen the tailing sand using the preset standard to obtain a tailing sand sample;
- a sample preserving module, which is configured to preserve the tailing sand sample;
- a tailing dam analyzing module, which is configured to evaluate the stability of the target tailing fill dam through the particle composition and the mechanical property.

\* \* \* \* \*